United States Patent [19]

Doria et al.

[11] Patent Number: 4,537,962
[45] Date of Patent: Aug. 27, 1985

[54] SUBSTITUTED 1,3,4-THIADIAZOLO[3,2-A]PYRIMIDINES AND COMPOSITIONS CONTAINING THEM

[75] Inventors: Gianfederico Doria, Milan; Carlo Passarotti, Gallarate; Ada Buttinoni, Milan, all of Italy

[73] Assignee: Farmitalia Carlo Erba, S.p.A., Milan, Italy

[21] Appl. No.: 459,188

[22] Filed: Jan. 19, 1983

[30] Foreign Application Priority Data

Feb. 4, 1982 [GB] United Kingdom ............... 8203238

[51] Int. Cl.³ .............. C07D 239/00; A61K 31/495
[52] U.S. Cl. ................................ 544/255; 548/136
[58] Field of Search ............... 544/255; 424/250; 542/441

[56] References Cited

U.S. PATENT DOCUMENTS

| 4,341,780 | 7/1982 | Doria et al. | 544/282 |
| 4,428,952 | 1/1984 | Doria et al. | 544/252 |
| 4,444,773 | 4/1984 | Doria et al. | 544/281 |

FOREIGN PATENT DOCUMENTS

| 28439 | 9/1975 | Japan | 544/255 |
| 42989 | 2/1981 | Japan | 544/255 |

OTHER PUBLICATIONS

Chem. Abst., vol. 79, 1973, p. 458, 32002z, Okabe.
Tsuji et al., Chem. Pharm. Bull., 19, 2530–2533, 1971.
Burger, Medicinal Chem., 2nd edition, pp. 42, 43.
Chemical Abstracts, vol. 76, 59562g, Tsuji et al., (1972).
Farm Doc DT 2712932 Grunenthal (1978).
Farm Doc Belgian 855334 Grunenthal (1977).
Patents Abstracts of Japan, vol. 4, No. 174, Dec. 2, 1980, (Japanese Pat. No. 55,115889).

*Primary Examiner*—Donald G. Daus
*Assistant Examiner*—Cecilia Shen
*Attorney, Agent, or Firm*—Murray, Whisenhunt and Ferguson

[57] ABSTRACT

Compounds of the formula (I)

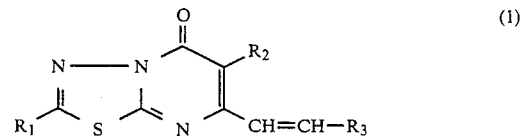

wherein $R_1$ is
(a) hydrogen or halogen;
(b) a $C_1$–$C_6$ alkyl group, unsubstituted or substituted by $C_1$–$C_4$ alkoxy or by halogen;
(c) a phenyl ring unsubstituted or substituted by a group chosen from halogen, $C_1$–$C_4$ alkyl and $C_1$–$C_4$ alkoxy;
(d) a $C_1$–$C_6$ alkylthio group;

$R_2$ is hydrogen or halogen;

$R_3$ is 2-pyridyl, 3-pyridyl or 4-pyridyl, wherein each pyridyl group is unsubstituted or substituted by $C_1$–$C_4$ alkyl; and the pharmaceutically acceptable salts thereof. The compounds possess anti-ulcerogenic and gastric anti-secretory activity.

3 Claims, No Drawings

SUBSTITUTED 1,3,4-THIADIAZOLO[3,2-A]PYRIMIDINES AND COMPOSITIONS CONTAINING THEM

The present invention relates to substituted 1,3,4-thiadiazolo[3,2-a]pyrimidines, to a process for their preparation and to pharmaceutical compositions containing them.

The invention provides compounds having the following general formula (I)

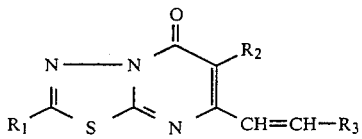

wherein
$R_1$ is (a) hydrogen or halogen;

(b) a $C_1-C_6$ alkyl group, unsubstituted or substituted by $C_1-C_4$ alkoxy or by one, two or three halogen atoms;

(c) a thienyl or phenyl ring, wherein the phenyl ring is unsubstituted or substituted by one or two substituents chosen from halogen, $C_1-C_4$ alkyl, hydroxy, $C_1-C_4$ alkoxy, formyloxy, $C_2-C_8$ alkanoyloxy, nitro, amino, di-($C_1-C_4$)-alkylamino, formylamino and $C_2-C_8$ alkanoylamino;

(d) a $C_1-C_6$ alkylthio group or a benzylthio group, wherein the phenyl ring is unsubstituted or substituted by one or two substituents chosen from halogen, $C_1-C_4$ alkyl and $C_1-C_4$ alkoxy;

$R_2$ is hydrogen, halogen, hydroxy, $C_1-C_6$ alkyl, $C_3-C_4$ alkenyl, $C_1-C_6$ alkoxy, $C_3-C_4$ alkenyloxy, formyloxy or $C_2-C_8$ alkanoyloxy;

$R_3$ is:

(a″) a group of formula

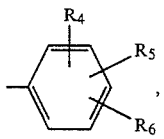

wherein each of $R_4$, $R_5$ and $R_6$ independently is (a‴) a hydrogen or halogen atom; (b‴) a trihalo-$C_1-C_6$ alkyl group; (c‴) hydroxy or a $C_1-C_6$ alkoxy group unsubstituted or substituted by a di-($C_1-C_4$)alkylamino group; (d‴) a $C_1-C_4$ alkyl group; (e‴) a formyloxy or $C_2-C_8$ alkanoyloxy group; (f‴) a —$NO_2$ or

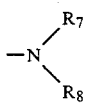

group, wherein each of $R_7$ and $R_8$ independently represents a hydrogen atom, a $C_1-C_4$ alkyl group, a formyl or a $C_2-C_8$ alkanoyl group; or (b″) a heterocyclic ring chosen from the group consisting of pyridyl, thiazolyl, furyl, thienyl and pyrrolyl, wherein the heterocyclic ring is unsubstituted or substituted by $C_1-C_4$ alkyl; and the pharmaceutically acceptable salts thereof.

The present invention includes all the possible isomers of the compounds of formula (I), e.g., cis or trans isomers and optical isomers, and the mixtures thereof. Preferably the —CH=CH—$R_3$ moiety, wherein $R_3$ is as defined above, is in the trans configuration.

The alkyl, alkenyl, alkoxy, alkenyloxy, alkylthio, trihaloalkyl, alkylamino, alkanoylamino and alkanoyloxy groups may be branched or straight chain groups.

A halogen atom is for example chlorine, fluorine or bromine, preferably it is chlorine or fluorine.

A $C_1-C_6$ alkyl group is preferably a $C_1-C_4$ alkyl group, in particular, methyl, ethyl, propyl, or isopropyl.

A $C_1-C_4$ alkyl group is preferably methyl, ethyl, propyl or isopropyl.

A $C_1-C_6$ alkoxy group is preferably a $C_1-C_4$ alkoxy group, in particular, methoxy, ethoxy, propoxy or isopropoxy.

A $C_1-C_4$ alkoxy group is preferably methoxy, ethoxy, propoxy or isopropoxy.

A $C_2-C_8$ alkanoyloxy group is preferably a $C_2-C_6$ alkanoyloxy group, in particular, acetyloxy, propionyloxy, butyryloxy, valeryloxy and isovaleryloxy; and more preferably it is acetyloxy or propionyloxy.

A di-($C_1-C_4$)-alkylamino group is, for example, N,N-dimethylamino, N,N-diethylamino and N-methyl-N-ethylamino, preferably it is a N,N-dimethylamino or N,N-diethylamino group.

A $C_2-C_8$ alkanoylamino group is preferably a $C_2-C_6$ alkanoylamino group, in particular acetylamino, propionylamino and butyrylamino, more preferably it is acetylamino or propionylamino.

A $C_1-C_6$ alkylthio group is preferably a $C_1-C_4$ alkylthio group, in particular methylthio or ethylthio.

A trihalo-$C_1-C_6$ alkyl group is, for example, a trifluoro-$C_1-C_6$ alkyl group, in particular it is trifluoro-$C_1-C_4$ alkyl, preferably trifluoromethyl.

A $C_2-C_8$ alkanoyl group is preferably a $C_2-C_6$ alkanoyl group, in particular acetyl, propionyl, valeryl and isovaleryl, more preferably it is acetyl or propionyl.

When $R_1$ and/or $R_2$ are a $C_1-C_6$ alkyl group, they are preferably a methyl, ethyl, propyl or isopropyl group. When $R_1$ and/or $R_2$ are halogen they are preferably chlorine, bromine or fluorine.

When $R_1$ is a $C_1-C_6$ alkyl group substituted by a $C_1-C_4$ alkoxy group, it is preferably a $C_1-C_4$ alkyl group substituted by a $C_1-C_3$ alkoxy group, in particular it is methoxy-methyl, ethoxy-methyl, methoxy-ethyl, ethoxy-ethyl, isopropoxy-methyl or isopropoxy-ethyl.

When $R_1$ is $C_1-C_6$ alkyl substituted by one, two or three halogen atoms, it is preferably a trihalo-$C_1-C_4$ alkyl group, in particular a trifluoro-$C_1-C_4$ alkyl group, more preferably a trifluoromethyl group.

When $R_1$ is a phenyl ring substituted by one or two halogen atoms, they are preferably chlorine or fluorine.

When $R_1$ is a phenyl ring substituted by one or two $C_1-C_4$ alkyl groups, they are preferably methyl or ethyl groups.

When $R_1$ is a phenyl ring substituted by one or two $C_1-C_4$ alkoxy groups, they are preferably methoxy or ethoxy groups.

When $R_1$ is a phenyl ring substituted by one or two $C_2-C_8$ alkanoyloxy groups, they are preferably acetyloxy or propionyloxy.

When $R_1$ is a phenyl ring substituted by one or two di($C_1$–$C_4$)-alkylamino groups, they are preferable N,N-dimethylamino or N,N-diethylamino.

When $R_1$ is a phenyl ring substituted by one or two $C_2$–$C_8$ alkanoylamino groups, they are preferably acetylamino or propionylamino.

When $R_1$ is a $C_1$–$C_6$ alkylthio group, it is preferably a methylthio or ethylthio group.

When $R_1$ is a benzylthio group, wherein the phenyl ring is substituted by one or two halogen atoms, they are preferably chlorine or fluorine.

When $R_1$ is a benzylthio group, wherein the phenyl ring is substituted by one or two $C_1$–$C_4$ alkyl groups, they are preferably methyl or ethyl.

When $R_1$ is a benzylthio group, wherein the phenyl ring is substituted by one or two $C_1$–$C_4$ alkoxy groups, they are preferably methoxy or ethoxy.

When $R_2$ is a $C_1$–$C_6$ alkoxy group, it is preferably a methoxy or ethoxy.

When $R_2$ is a $C_2$–$C_8$ alkanoyloxy group, it is preferably acetyloxy or propionyloxy.

When one or more of $R_4$, $R_5$ and $R_6$ is a halogen atom, it is preferably chlorine or fluorine.

When one or more of $R_4$, $R_5$ and $R_6$ is a trihalo-$C_1$–$C_6$ alkyl group, it is preferably a trifluoromethyl group.

When one or more of $R_4$, $R_5$ and $R_6$ is a $C_1$–$C_6$ alkoxy group unsubstituted or substituted by a di-($C_1$–$C_4$)-alkylamino group, it is preferably a methoxy, ethoxy or propoxy group unsubstituted or substituted by a N,N-dimethylamino or N,N-diethylamino group.

When one or more of $R_4$, $R_5$ and $R_6$ is a $C_1$–$C_4$ alkyl group, it is preferably a methyl group.

When one or more of $R_4$, $R_5$ and $R_6$ is a $C_2$–$C_8$ alkanoyloxy group, it is preferably acetyloxy or propionyloxy.

When $R_7$ and/or $R_8$ are $C_1$–$C_4$ alkyl, the alkyl group is preferably methyl or ethyl.

When $R_7$ and $R_8$ are a $C_2$–$C_8$ alkanoyl group, the alkanoyl group is preferably acetyl.

When $R_3$ is a heterocyclic ring as defined above under (b″), it is preferably chosen from pyridyl, thiazolyl and thienyl and the heterocyclic ring is unsubstituted or preferably substituted by a methyl group; or said heterocyclic ring is a pyrrolyl ring substituted by $C_1$–$C_4$ alkyl wherein preferably the substituent is a N-($C_1$–$C_4$) alkyl substituent, in particular a N-methyl or a N-ethyl substituent.

Preferred compounds of the invention are the compounds having formula (I), wherein $R_1$ is hydrogen, chlorine, methyl, ethyl, methylthio, ethylthio, trifluoromethyl, methoxymethyl, ethoxymethyl, benzylthio, thienyl or a phenyl ring unsubstituted or substituted by one or two substituents chosen from methyl, methoxy, chlorine, fluorine, amino, acetylamino and N,N-diethylamino;

$R_2$ is hydrogen, methyl, methoxy, fluorine or chlorine;

$R_3$ is a thienyl or pyridyl group unsubstituted or substituted by a methyl group; or $R_3$ is a phenyl ring unsubstituted or substituted by one or two substituents chosen from the group including chlorine, fluorine, $C_1$–$C_4$ alkyl, trifluoromethyl, hydroxy, amino, acetylamino, acetoxy or $C_1$–$C_4$ alkoxy unsubstituted or substituted by a N,N-dimethylamino group; and the pharmaceutically acceptable salts thereof.

Examples of pharmaceutically acceptable salts are those with inorganic acids, e.g. hydrochloric, hydrobromic, nitric and sulphuric acids and with organic acids, e.g. citric, tartaric, maleic, malic, fumaric, methanesulphonic and ethanesulphonic acids. Examples of particularly preferred compounds of the invention are:

2-phenyl-7-trans-[2-(3-pyridyl)-ethenyl]-5H-1,3,4-thiadiazolo[3,2-a]pyrimidine-5-one;

2-(4-fluoro-phenyl)-7-trans-[2-(3-pyridyl)-ethenyl]-5H-1,3,4-thiadiazolo[3,2-a]pyrimidine-5-one;

2-(4-methyl-phenyl)-7-trans-[2-(3-pyridyl)-ethenyl]-5H-1,3,4-thiadiazolo[3,2-a]pyrimidine-5-one;

2-(4-amino-phenyl)-7-trans-[2-(3-pyridyl)-ethenyl]-5H-1,3,4-thiadiazolo[3,2-a]pyrimidine-5-one;

2-(2-thienyl)-7-trans-[2-(3-pyridyl)-ethenyl]-5H-1,3,4-thiadiazolo[3,2-a]pyrimidine-5-one;

2-benzylthio-7-trans-[2-(3-pyridyl)-ethenyl]-5H-1,3,4-thiadiazolo[3,2-a]pyrimidine-5-one;

2-phenyl-7-trans-[2-(6-methyl-2-pyridyl)-ethenyl]-5H-1,3,4-thiadiazolo[3,2-a]pyrimidine-5-one;

2-(4-fluoro-phenyl)-7-trans-[2-(6-methyl-2-pyridyl)-ethenyl]-5H-1,3,4-thiadiazolo[3,2-a]pyrimidine-5-one;

2-phenyl-7-trans-[2-(2-pyridyl)-ethenyl]-5H-1,3,4-thiadiazolo[3,2-a]pyrimidine-5-one;

2-phenyl-7-trans-[2-(4-pyridyl)-ethenyl]-5H-1,3,4-thiadiazolo[3,2-a]pyrimidine-5-one;

2-(4-acetylamino-phenyl)-7-trans-[2-(3-pyridyl)-ethenyl]-5H-1,3,4-thiadiazolo[3,2-a]pyrimidine-5-one;

2-(3-chloro-phenyl)-7-trans-[2-(3-pyridyl)-ethenyl]-5H-1,3,4-thiadiazolo[3,2-a]pyrimidine-5-one;

2-methyl-7-trans-[2-(3-pyridyl)-ethenyl]-5H-1,3,4-thiadiazolo[3,2-a]pyrimidine-5-one;

2-ethyl-7-trans-[2-(3-pyridyl)-ethenyl]-5H-1,3,4-thiadiazolo[3,2-a]pyrimidine-5-one;

2-methoxymethyl-7-trans-[2-(3-pyridyl)-ethenyl]-5H-1,3,4-thiadiazolo[3,2-a]pyrimidine-5-one;

2-methoxymethyl-7-trans-[2-(4-fluoro-phenyl)-ethenyl]-5H-1,3,4-thiadiazolo[3,2-a]pyrimidine-5-one;

7-trans-(2-phenyl-ethenyl)-5H-1,3,4-thiadiazolo[3,2-a]pyrimidine-5-one;

7-trans-[2-(4-fluoro-phenyl)-ethenyl]-5H-1,3,4-thiadiazolo[3,2-a]pyrimidine-5-one;

7-trans-[2-(3-fluoro-phenyl)-ethenyl]-5H-1,3,4-thiadiazolo[3,2-a]pyrimidine-5-one;

7-trans-[2-(2-fluoro-phenyl)-ethenyl]-5H-1,3,4-thiadiazolo[3,2-a]pyrimidine-5-one;

2-chloro-7-trans-(2-phenyl-ethenyl)-5H-1,3,4-thiadiazolo[3,2-a]pyrimidine-5-one;

2-chloro-7-trans-[2-(4-fluoro-phenyl)-ethenyl]-5H-1,3,4-thiadiazolo[3,2-a]pyrimidine-5-one;

7-trans-[2-(4-chloro-phenyl)-ethenyl]-5H-1,3,4-thiadiazolo[3,2-a]pyrimidine-5-one;

7-trans-[2-(4-acetoxy-phenyl)-ethenyl]-5H-1,3,4-thiadiazolo[3,2-a]pyrimidine-5-one;

and the pharmaceutically acceptable salts thereof.

The compounds of the invention are prepared by a process comprising:

(a) reacting a compound of formula (II)

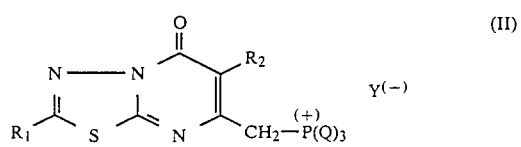

wherein $R_1$ and $R_2$ are as defined above, Q may be aryl, or $C_1$–$C_6$ alkyl, and $Y^{(-)}$ represents an acidic anion, with an aldehyde of formula (III)

wherein $R_3$ is as defined above; or (b) reacting a compound of formula (IV)

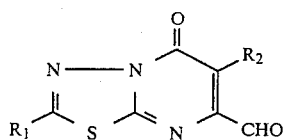 (IV)

wherein $R_1$ and $R_2$ are as defined above, with a compound of formula (V)

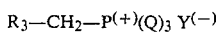 (V)

wherein $R_3$, Q and $Y^{(-)}$ are as defined above, or alternatively with a compound of formula (VI)

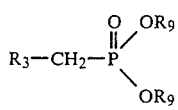 (VI)

wherein $R_3$ is as defined above and each of $R_9$, being the same or different, is $C_1$–$C_4$ alkyl;

and, if desired, converting a compound of formula (I) into another compound of formula (I) and/or if desired, converting a compound of formula (I) into a pharmaceutically acceptable salt and/or, if desired, obtaining a free compound of formula (I) from a salt thereof and/or, if desired, separating a mixture of isomers into the single isomers.

The acidic anion $Y^{\ominus}$ in the compounds of formula (II) and (V) is, for example, an acidic anion deriving from a hydrohalic acid, preferably, deriving from hydrochloric or hydrobromic acid.

When Q in the compounds of formula (II) and (V) is aryl, it is preferably phenyl; and when Q is $C_1$–$C_6$ alkyl, it is preferably ethyl.

The reaction between a compound of formula (II) and an aldehyde of formula (III) as well as the reaction of a compound of formula (IV) with a compound of formula (V) or with a compound of formula (VI), may, for example, be carried out by treatment with a base such as dimethylsulphinyl carbanion or sodium methoxide or sodium hydride or potassium terbutoxide or with an alkyl-lithium or an aryl-lithium derivative, preferably with methyl-lithium or butyl-lithium or phenyl-lithium, in an organic solvent such as dichloromethane, dichlorethane, benzene, toluene, tetrahydrofuran, dimethylsulfoxide, dimethylformamide, dimethylacetamide or their mixtures at a temperature varying from about 0° C. to about 100° C.

A compound of formula (I) may be converted, as stated above, into another compound of formula (I) by known methods; for example, free hydroxy groups may be etherified by reacting with a suitable alkyl halide in the presence of a base such $NaHCO_3$, $KHCO_3$, $Na_2CO_3$, $K_2CO_3$, in a solvent selected from the group consisting, for example, of methanol, ethanol, dioxane, acetone, dimethylformamide, hexamethylphosphorotriamide, tetrahydrofuran, water and their mixtures at a temperature ranging preferably between about 0° C. and about 150° C. Furthermore a hydroxy or an amino group, for example, may be converted respectively into a $C_2$–$C_8$ alkanoyloxy or $C_2$–$C_8$ alkanoylamino group using conventional methods well known in organic chemistry.

A nitro group as substituent in a phenyl ring in a compound of formula (I) may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

Also the optional salification of a compound of formula (I) as well as the conversion of a salt into the free compound and the separation of a mixture of isomers into the single isomers may be carried out by conventional methods. For example the separation of a mixture of optical isomers into the individual isomers may be carried out by salification with an optically active acid and subsequent fractional crystallization.

Thus the separation of a mixture of geometric isomers may be carried out, for example, by fractional crystallization. The compounds of formula (II) may be prepared, for example, by reacting a compound of formula (VII)

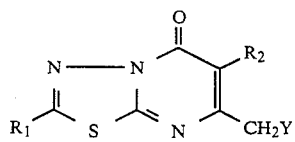 (VII)

wherein Y is a radical capable of being converted to an anion $Y^{(-)}$ as defined above and $R_1$ and $R_2$ are as defined above, with $P(Q)_3$, wherein Q is as defined above, in a solvent such as benzene, toluene, xylene or acetonitrile at a temperature varying between room temperature and the reflux temperature.

The compounds of formula (IV) may be prepared, for example, by oxidizing a compound of formula (VIII)

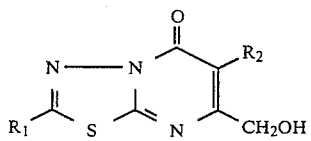 (VIII)

wherein $R_1$ and $R_2$ are as defined above, for example, with dimethylsulfoxide in the presence of dicyclohexylcarbodiimide and phosphoric acid or pyridinium-trifluoroacetate (Moffat reaction) in a solvent such as benzene, toluene or dimethylsulfoxide at a temperature varying between 0° C. and 50° C.

The compounds of formula (VII) wherein Y is halogen and $R_2$ is hydrogen may, for example, be prepared by reacting a compound of formula (IX)

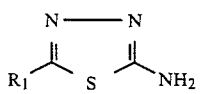 (IX)

wherein $R_1$ is as defined above, with a compound of formula (X)

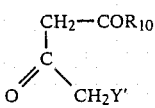

(X)

wherein $R_{10}$ is $C_1$-$C_6$ alkoxy and $Y'$ represents a halogen atom, preferably chlorine.

The reaction between a compound of formula (IX) and a compound of formula (X) may, for example, be carried out in the presence of an acid condensing agent such as polyphosphoric acid (polyphosphoric acid means a mixture of about equal weights of 99% $H_3PO_4$ and $P_2O_5$), sulphuric acid, methanesulphonic acid or p-toluenesulphonic acid, at a temperature ranging preferably between about 50° C. and 150° C.; the reaction may be carried out in an organic solvent such as dimethylformamide, dimethylacetamide, acetic acid, formic acid, benzene, toluene, xylene, ethylene glycol monomethylether or dichloroethane, but it is preferably carried out in the absence of a solvent.

The compounds of formula (VII) wherein $R_2$ is different from hydrogen, may be prepared, for example, from a compound of formula (XI)

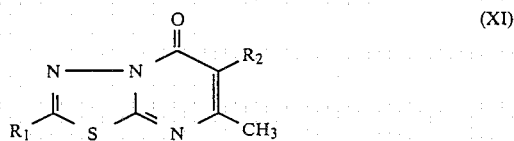

(XI)

wherein $R_1$ and $R_2$ are as defined above, provided that the group $R_2$ is other than hydrogen, by reaction with a N-halosuccinimide, preferably N-bromosuccinimide, in a solvent such as benzene or $CCl_4$ at a temperature varying between room temperature and the reflux temperature.

Alternatively the compound of formula (VII) wherein $R_2$ is chlorine or bromine may be prepared by reacting a compound of formula (VII) wherein $R_2$ is hydrogen with $SO_2Cl_2$ or pyridinium bromide perbromide respectively, operating at a temperature ranging from 0° C. to 100° C. and using, for example, as solvent $CCl_4$ or dichloroethane in the reaction with $SO_2Cl_2$ and pyridine in the reaction with pyridinium bromide perbromide.

The compounds of formula (VIII) may be prepared, for example, by reacting a compound of formula (VII) wherein Y, being as defined above, is a good leaving group, for example, Cl or Br, with potassium or sodium acetate in dimethylformamide at a temperature varying between room temperature and 100° C., so obtaining the corresponding acetoxy-derivative, which in turn is hydrolysed to the corresponding alcohol (VIII), for example, by treatment with 37% HCl in dioxane at a temperature varying between room temperature and the reflux temperature.

The compounds of formula (XI) may be prepared, for example, by reacting a compound of formula (IX) with a compound of formula (XII)

(XII)

wherein $R_2$ and $R_{10}$ are as defined above, using the same experimental conditions as defined above for the reaction between a compound of formula (IX) and a compound of formula (X). The compounds of formula (III), (V), (VI), (IX), (X) and (XII) are known compounds and may be prepared by conventional methods: in some cases they are commercially available products.

The compounds of the present invention are active on the gastroenteric system, in particular they are endowed with anti-ulcerogenic and gastric anti-secretory activity and are therefore useful in therapy, for example in the prevention and treatment of peptic, e.g. duodenal, gastric and exophageal ulcers and to inhibit gastric acid secretion. The compounds of the invention are also useful for reducing the undesirable gastrointestinal side-effects resulting from systemic administration of anti-inflammatory prostaglandin synthetase inhibitors and may be, therefore, used for this purpose in association with them. The anti-ulcerogenic activity of the compounds of the invention is shown, e.g., by the fact that they are active in the test of the inhibition of restraint ulcers in rats, according to the method of Bonfils et al., (Thérapie, 1960, 15, 1096; Jap. J. Pharmac. 1968, 18, 9).

Six Sprague-Dawley male rats (100-120 g) fasted 24 hours were used for the experiment: a square flexible small-mesh wire netting was used for the immobilization and 4 hours after the immobilization the rats were sacrificed, their stomachs were removed and the lesions counted under a dissecting microscope. The tested compounds were administered per os (p.o.) one hour before the immobilization. The following Table I shows, for example, the approximate $ED_{50}$ value of the anti-ulcerogenic activity obtained in the above test in the rat after oral administration for one of the preferred compounds of this invention:

TABLE 1

| Compound | Antiulcerogenic activity p.o. |
|---|---|
| 2-phenyl-7-trans-[2-(3-pyridyl)-ethenyl]-5H—1,3,4-thiadiazolo[3,2-a]pyrimidine-5-one | $ED_{50}$ = 3 mg/kg |

The compounds of the invention own also gastric antisecretory activity as shown, e.g., by the fact that they proved to be active, after intraduodenal administration, in inhibiting the gastric secretion in rats according to the method of H. Shay et al. (Gastroenter., 1945, 43, 5). Gastric antisecretory activity was evaluated in rats by the pylorus ligature technique. Six Sprague-Dawley male rats (110-130 g) were used for each group. Twenty-four hours before the test, the rats were deprived of food but their water supply was maintained. On the day of the operation, the pylorus was ligated under light ether anaesthesia. Each compound was injected intraduodenally (i.d.) at the time of the ligature. Four hours after the ligature the rats were sacrificed, the stomach secretion was collected and centrifuged at 3500 r.p.m. for 10 minutes, and the volume, less sediment, was determined.

The amount of the free hydrochloric acid in the gastrc juice was determined by titration against 0.01N sodium hydroxide to pH 7.0 on the pH-meter.

One of the preferred compounds of this invention having gastric antisecretory activity is, for example, the compound 2-(4-methyl-phenyl)-7-trans-[2-(3-pyridyl)-ethenyl]-5H-1,3,4-thiadiazolo[3,2-a]pyrimidine-5-one, which has an approximate $ED_{50}$ value of 50 mg/kg in the above test in the rat, after intraduodenal administration.

The compounds of this invention possess also anti-inflammatory activity as demonstrated e.g. by the fact that they are active, after oral administration, in inhibiting:

(A) the edema formation on the hind paw of rats in response to a subplantar injection of carrageenin, according to the method of C. A. Winter et al. (J. Pharmac. Exp. Therap. 1963, 141, 369) and P. Lence (Arch. Int. Pharmacodyn., 1962, 136, 237), and (B) the Reversed Passive Arthus Reaction (RPAR) in rat paw, induced by the interaction of antigen and antibody resulting in the formation of precipitating immune complex, followed by fixation of complement and accumulation of polymorphonuclear leucocytes at a focal point (D. K. Gemmell, J. Cottney and A. J. Lewis, Agents and Actions 9/1 pag. 107, 1979).

The compounds of this invention are also endowed with analgesic activity. The analgesic activity was assessed, for example, by means of phenyl quinone test in mice according to Siegmund: [Siegmund et al. Proc. Soc. Exper. Biol. Med. 95, 729 (1957)]. Therefore the compounds of the invention may be used in therapy to treat inflammatory processes, such as rheumatoid arthritis and osteoarthrosis and as analgesics.

As examples of compounds having antiinflammatory and/or analgesic activity the following can be mentioned: 7-trans-(2-phenyl-ethenyl)-5H-1,3,4-thiadiazolo[3,2-a]pyrimidine-5-one and 7-trans-[2-(4-fluoro-phenyl)-ethenyl]-5H-1,3,4-thiadiazolo[3,2-a]pyrimidine-5-one.

In view of their high therapeutic index, the compounds of the invention can be used safely in medicine. For example, the approximate acute toxicity ($LD_{50}$) of the compounds 7-trans-(2-phenyl-ethenyl)-5H-1,3,4-thiadiazolo[3,2-a]pyrimidine-5-one, 2-methyl-7-trans-(2-phenyl-ethenyl)-5H-1,3,4-thiadiazolo[3,2-a]pyrimidine-5-one, 7-trans-[2-(2,6-dichloro-phenyl)-ethenyl]-5H-1,3,4-thiadiazolo[3,2-a]pyrimidine-5-one, 7-trans-[2-(3-pyridyl)-ethenyl]-5H-1,3,4-thiadiazolo[3,2-a]pyrimidine-5-one, 7-trans-[2-(4-fluoro-phenyl)-ethenyl]-5H-1,3,4-thiadiazolo[3,2-a]pyrimidine-5-one, 2-phenyl-7-trans-[2-(3-pyridyl)-ethenyl]-5H-1,3,4-thiadiazolo[3,2-a]pyrimidine-5-one and 2-(4-methyl-phenyl)-7-trans-[2-(3-pyridyl)-ethenyl]-5H-1,3,4-thiadiazolo[3,2-a]pyrimidine-5-one in the mouse, determined by single administration of increasing doses and measured on the seventh day after the day of treatment, is higher than 800 mg/kg per os. Analogous toxicity data have been found for the other compounds of the invention.

The compounds of the invention can be administered in a variety of dosage forms, e.g. orally, in the form of tablets, capsules, sugar or film coated tablets, liquid solutions or suspensions, rectally, in the form of suppositories, parenterally, e.g. intramuscularly, or by intravenous injection or infusion. The dosage depends on the age, weight, conditions of the patient and administration route; for example the dosage adopted for oral administration to adult humans ranges from about 50 to about 200 mg per dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

2-amino-1,3,4-thiadiazole (5 g) was reacted with ethyl 4-chloro-acetoacetate (12.3 g) in polyphosphoric acid (25 g) under stirring at 100° C. for 2 hours.

After cooling, dilution with ice water and neutralization with 35% NaOH, the precipitate was filtered and washed with water until neutral to give 7-chloromethyl-5H-1,3,4-thiadiazolo[3,2-a]pyrimidine-5-one, m.p. 194°–196° C. (9 g), which was reacted with triphenylphosphine (12.6 g) in acetonitrile (90 ml) under stirring at reflux temperature for 30 hours. After cooling the precipitate was filtered and washed with ethyl acetate to give (5-oxo-5H-1,3,4-thiadiazolo[3,2-a]pyrimidine-7-yl)-methyl-triphenylphosphonium chloride, m.p. 230°–240° C. dec (20.5 g), which was suspended in dimethylsulphoxide (60 ml) and treated dropwise with potassium terbutoxide (4.9 g) dissolved in dimethylsulphoxide (40 ml) at a temperature of about 20° C. The solution of the ylide so obtained was then reacted with benzaldehyde (5.5 g) at room temperature for 30 minutes. After dilution with ice water the precipitate was filtered and washed with water: crystallization from CH$_2$Cl$_2$-acetone gave 4.4 g of 7-trans-(2-phenyl-ethenyl)-5H-1,3,4-thiadiazolo[3,2-a]pyrimidine-5-one, m.p. 217°–219° C., N.M.R. (CDCl$_3$) δp.p.m.: 6.39 (s) (1H, C-6 proton), 6.90 (d) (1H, β-ethenyl proton), 7.30–7.67 (m) (5H, phenyl protons), 7.80 (d) (1H, α-ethenyl proton), 8.73 (s) (1H, C-2 proton); $J_{H\alpha H\beta}=16$ Hz.

By proceeding analogously the following compounds were prepared:

7-trans-[2-(2-methyl-phenyl)-ethenyl]-5H-1,3,4-thiadiazolo[3,2-a]pyrimidine-5-one, m.p. 268°–272° C.;

7-trans-[2-(3-methyL-phenyl)-ethenyl]-5H-1,3,4-thiadiazolo[3,2-a]pyrimidine-5-one, m.p. 214°–215° C.;

7-trans-[2-(4-methyl-phenyl)-ethenyl]-5H-1,3,4-thiadiazolo[3,2-a]pyrimidine-5-one, m.p. 244°–247° C.;

7-trans-[2-(2,5-dimethyl-phenyl)-ethenyl]-5H-1,3,4-thiadiazolo[3,2-a]pyrimidine-5-one;

7-trans-[2-(2,4-dimethyl-phenyl)-ethenyl]-5H-1,3,4-thiadiazolo[3,2-a]pyrimidine-5-one;

7-trans-[2-(2-methoxy-phenyl)-ethenyl]-5H-1,3,4-thiadiazolo[3,2-a]pyrimidine-5-one, m.p. 260°–265° C. dec.;

7-trans-[2-(3-methoxy-phenyl)-ethenyl]-5H-1,3,4-thiadiazolo[3,2-a]pyrimidine-5-one, m.p. 211°–212° C.;

7-trans-[2-(4-methoxy-phenyl)-ethenyl]-5H-1,3,4-thiadiazolo[3,2-a]pyrimidine-5-one;

7-trans-[2-(2,3-dimethoxy-phenyl)-ethenyl]-5H-1,3,4-thiadiazolo[3,2-a]pyrimidine-5-one, m.p. 219°–221° C.;

7-trans-[2-(2,5-dimethoxy-phenyl)-ethenyl]-5H-1,3,4-thiadiazolo[3,2-a]pyrimidine-5-one;

7-trans-[2-(3,4-dimethoxy-phenyl)-ethenyl]-5H-1,3,4-thiadiazolo[3,2-a]pyrimidine-5-one, m.p. 235°–245° C. dec.;

7-trans-[2-(2,4-dimethoxy-phenyl)-ethenyl]-5H-1,3,4-thiadiazolo[3,2-a]pyrimidine-5-one;

7-trans-[2-(3,5-dimethoxy-phenyl)-ethenyl]-5H-1,3,4-thiadiazolo[3,2-a]pyrimidine-5-one;

7-trans-[2-(2-methoxy-3-ethoxy-phenyl)-ethenyl]-5H-1,3,4-thiadiazolo[3,2-a]pyrimidine-5-one;

7-trans-{2-[4-(3-N,N-dimethylamino-propoxy)-phenyl]ethenyl}-5H-thiadiazolo[3,2-a]pyrimidine-5-one;

7-trans-[2-(4-fluoro-phenyl)-ethenyl]-5H-1,3,4-thiadiazolo[3,2-a]pyrimidine-5-one, m.p. 254°–256° C.;

7-trans-[2-(3-fluoro-phenyl)-ethenyl]-5H-1,3,4-thiadiazolo[3,2-a]pyrimidine-5-one, m.p. 227°–229° C.;

7-trans-[2-(2-fluoro-phenyl)-ethenyl]-5H-1,3,4-thiadiazolo[3,2-a]pyrimidine-5-one, m.p. 238°–241° C.;

7-trans-[2-(4-nitro-phenyl)-ethenyl]-5H-1,3,4-thiadiazolo[3,2-a]pyrimidine-5-one;

7-trans-[2-(4-hydroxy-phenyl)-etheny]-5H-1,3,4-thiadiazolo[3,2-a]pyrimidine-5-one;

7-trans-[2-(2-chloro-phenyl)-ethenyl]-5H-1,3,4-thiadiazolo[3,2-a]pyrimidine-5-one;

7-trans-[2-(3-chloro-phenyl)-ethenyl]-5H-1,3,4-thiadiazolo[3,2-a]pyrimidine-5-one;

7-trans-[2-(4-chloro-phenyl)-ethenyl]-5H-1,3,4-thiadiazolo[3,2-a]pyrimidine-5-one, m.p. 234°–236° C.;

7-trans-[2-(2,4-dichloro-phenyl)-ethenyl]-5H-1,3,4-thiadiazolo[3,2-a]pyrimidine-5-one;

7-trans-[2-(2,6-dichloro-phenyl)ethenyl]-5H-1,3,4-thiadiazolo[3,2-a]pyrimidine-5-one, m.p. 260°–270° C. dec.;

7-trans-[2-(3,4-dichloro-phenyl)-ethenyl]-5H-1,3,4-thiadiazolo[3,2-a]pyrimidine-5-one;

7-trans-[2-(3-trifluoromethyl-phenyl)-ethenyl]-5H-1,3,4-thiadiazolo[3,2-a]pyrimidine-5-one; and 7-trans-[2-(4-acetoxy-phenyl)-ethenyl]-5H-1,3,4-thiadiazolo[3,2-a]pyrimidine-5-one, m.p. 249°–251° C.

EXAMPLE 2

By proceeding according to Example 1, using suitable heterocyclic aldehydes to replace the benzaldehyde, the following compounds were prepared:

7-trans-[2-(3-pyridyl)-ethenyl]-5H-1,3,4-thiadiazolo[3,2-a]pyrimidine-5-one, m.p. 245°–253° C. dec.;

7-trans-[2-(4-pyridyl)-ethenyl]-5H-1,3,4-thiadiazolo[3,2-a]pyrimidine-5-one;

7-trans-[2-(6-methyl-2-pyridyl)-ethenyl]-5H-1,3,4-thiadiazolo[3,2-a]pyrimidine-5-one;

7-trans-[2-(2-furyl)-ethenyl]-5H-1,3,4-thiadiazolo[3,2-a]pyrimidine-5-one;

7-trans-[2-(2-methyl-5-thiazolyl)-ethenyl]-5H-1,3,4-thiadiazolo[3,2-a]pyrimidine-5-one;

7-trans-[2-(1-methyl-2-pyrrolyl)-ethenyl]-5H-1,3,4-thiadiazolo[3,2-a]pyrimidine-5-one, m.p. 250°–255° C. dec.;

7-trans-[2-(2-thienyl)-ethenyl]-5H-1,3,4-thiadiazolo[3,2-a]pyrimidine-5-one, m.p. 219°–221° C.; and 7-trans-[2-(5-methyl-2-furyl)-ethenyl]-5H-1,3,4-thiadiazolo[3,2-a]pyrimidine-5-one.

EXAMPLE 3

2-amino-5-methylthio-1,3,4-thiadiazole (9.4 g) was reacted with ethyl 4-chloro-acetoacetate (15.8 g) in polyphosphoric acid (50 g) under stirring at 100° C. for 1 hour. After cooling, dilution with ice water and neutralization with 35% NaOH, the precipitate was filtered and washed with water until neutral to give 7-chloromethyl-2-methylthio-5H-1,3,4-thiadiazolo[3,2-a]pyrimidine-5-one, m.p. 168°–169° C. (12.4 g), which was reacted with triphenylphosphine (14.4 g) in acetonitrile (250 ml) under stirring at reflux temperature for 24 hours. After cooling the precipitate was filtered and washed with isopropyl ether to give (2-methylthio-5-oxo-5H-1,3,4-thiadiazolo[3,2-a]pyrimidine-7-yl)-methyl-triphenylphosphonium chloride (24 g), which was suspended in dimethylsulphoxide (100 ml) and treated dropwise with potassium terbutoxide (5 g) dissolved in dimethylsulphoxide (80 ml) at a temperature of about 20° C. The solution of the ylide so obtained was then reacted with benzaldehyde (4.65 g) at room temperature for 60 minutes. After dilution with ice water the precipitate was extracted with ethyl acetate and the organic solution was evaporated in vacuo to dryness: after purification over SiO$_2$ column with CHCl$_3$-hexane, crystallization from CH$_2$Cl$_2$-methanol gave 3.8 g of 2-methylthio-7-trans-(2-phenyl-ethenyl)-5H-1,3,4-thiadiazolo[3,2-a]pyrimidine-5-one, m.p. 180°–182° C., N.M.R. (CDCl$_3$) δp.p.m.: 2.82 (s) (3H, —SCH$_3$), 6.35 (s) (1H, C-6 proton), 6.70 (d) (1H, β-ethenyl proton), 7.2–7.7 (m) (5H, phenyl protons), 7.70 (d) (1H, α-ethenyl proton); $J_{H\alpha H\beta}=16$ Hz.

By proceeding analogously the following compounds were prepared:

2-ethylthio-7-trans-(2-phenyl-ethenyl)-5H-1,3,4-thiadiazolo[3,2-a]pyrimidine-5-one; and 2-propylthio-7-trans-(2-phenyl-ethenyl)-5H-1,3-4-
thiadiazolo[3,2-a]pyrimidine-5-one.

EXAMPLE 4

By proceeding according to Example 3, using suitable aromatic or heterocyclic aldehydes in place of benzaldehyde, the following compounds were prepared:

2-benzylthio-7-trans-(2-phenyl-ehenyl)-5H-1,3,4-thiadiazolo[3,2-a]pyrimidine-5-one;

2-benzylthio-7-trans-[2-(4-fluoro-phenyl)-ethenyl]-5H-1,3,4-thiadiazolo[3,2-a]pyrimidine-5-one, m.p. 180°–182° C.;

2-benzylthio-7-trans-[2-(3-pyridyl)-ethenyl]-5H-1,3,4-thiadiazolo[3,2-a]pyrimidine-5-one, m.p. 179°–181° C.;

2-methylthio-7-trans-[2-(3-pyridyl)-ethenyl]-5H-1,3,4-thiadiazolo[3,2-a]pyrimidine-5-one;

2-methylthio-7-trans-[2-(1-methyl-2-pyrrolyl)-ethenyl]-5H-1,3,4-thiadiazolo[3,2-a]pyrimidine-5-one;

2-benzylthio-7-trans-[2-(1-methyl-2-pyrrolyl)-ethenyl]-5H-1,3,4-thiadiazolo[3,2-a]pyrimidine-5-one;

2-benzylthio-7-trans-[2-(2-thienyl)-ethenyl]-5H-1,3,4-thiadiazolo[3,2-a]pyrimidine-5-one;

2-methylthio-7-trans-[2-(4-fluoro-phenyl)-ethenyl]-5H-1,3,4-thiadiazolo[3,2-a]pyrimidine-5-one;

2-[(4-fluoro-benzyl)-thio]-7-trans-[2-(3-pyridyl)-ethenyl]-5H-1,3,4-thiadiazolo[3,2-a]pyrimidine-5-one;

2-[(4-methyl-benzyl)-thio]-7-trans-[2-(3-pyridyl)-ethenyl]-5H-1,3,4-thiadiazolo[3,2-a]pyrimidine-5-one;

2-[(4-chloro-benzyl)-thio]-7-trans-[2-(3-pyridyl)-ethenyl]-5H-1,3,4-thiadiazolo[3,2-a]pyrimidine-5-one;

2-[(3-methoxy-benzyl)-thio]-7-trans-[2-(3-pyridyl)-ethenyl]-5H-1,3,4-thiadiazolo[3,2-a]pyrimidine-5-one;

2-[(2,6-dichloro-benzyl)-thio]-7-trans-[2-(3-pyridyl)-ethenyl]-5H-1,3,4-thiadiazolo[3,2-a]pyrimidine-5-one;

2-[(2,5-dimethyl-benzyl)-thio]-7-trans-[2-(3-pyridyl)-ethenyl]-5H-1,3,4-thiadiazolo[3,2-a]pyrimidine-5-one;

2-[(4-fluoro-benzyl)-thio]-7-trans-[2-(4-fluoro-phenyl)-ethenyl]-5H-1,3,4-thiadiazolo[3,2-a]pyrimidine-5-one;

2-[(4-methyl-benzyl)-thio]-7-trans-[2-(4-fluoro-phenyl)-ethenyl]-5H-1,3,4-thiadiazolo[3,2-a]pyrimidine-5-one; and 2-[(4-chloro-benzyl)-thio]-7-trans-[2-(4-fluoro-phenyl)-ethenyl]-5H-1,3,4-thiadiazolo[3,2-a]pyrimidine-5-one.

EXAMPLE 5

2-amino-5-phenyl-1,3,4-thiadiazole (10 g) was reacted with ethyl 4-chloro-acetoacetate (18.6 g) in polyphosphoric acid (100 g) under stirring at 100° C. for 1 hour. After cooling, dilution with ice water and neutralization with 35% NaOH, the precipitate was filtered and washed with water until neutral: crystallization from methanol gave 7-chloromethyl-2-phenyl-5H-1,3,4-thiadiazolo[3,2-a]pyrimidine-5-one, m.p. 201°–202° C. (11.6 g), which was reacted with triphenylphosphine (12.4 g) in acetonitrile (500 ml) under stirring at reflux temperature for 48 hours. After cooling the precipitate was filtered and washed with isopropyl ether to give (5-oxo-2-phenyl-5H-1,3,4-thiadiazolo[3,2-a]pyrimidine-7-yl)-methyl-triphenylphosphonium chloride, m.p. 295°–300° C. (20 g), which was suspended in dimethylsulphoxide (100 ml) and treated dropwise with potassium terbutoxide (5 g) dissolved in dimethylsulphoxide (100 ml) at a temperature of about 20° C. The solution of the ylide so obtained was then reacted with benzaldehyde (4.55 g) at room temperature for 90 minutes. After dilution with ice water the precipitate was filtered and washed with water: crystallization from methanol gave 5.1 g of 2-phenyl-7-trans-(2-phenyl-ethenyl)-5H-1,3,4-thiadiazolo[3,2-a]pyrimidine-5-one, m.p. 217°–219° C., N.M.R. (CDCl$_3$) δp.p.m.: 6.34 (s) (1H, C-6-proton), 6.82 (d) (1H, β-ethenyl proton), 7.58 (d) (1H,α-ethenyl proton), 7.12–7.98 (m) (10H, phenyl protons); $J_{H\alpha H\beta}$=16 Hz.

By proceeding analogously the following compounds were prepared:

2-(4-methyl-phenyl)-7-trans-(2-phenyl-ethenyl)-5H-1,3,4-thiadiazolo[3,2-a]pyrimidine-5-one;

2-(3-methoxy-phenyl)-7-trans-(2-phenyl-ethenyl)-5H-1-3-4-thiadiazolo[3,2-a]pyrimidine-5-one;

2-(4-methoxy-phenyl)-7-trans-(2-phenyl-ethenyl)-5H-1,3,4-thiadiazolo[3,2-a]pyrimidine-5-one;

2-(3-chloro-phenyl)-7-trans-(2-phenyl-ethenyl)-5H-1,3,4-thiadiazolo[3,2-a]pyrimidine-5-one;

2-(4-chloro-phenyl)-7-trans-(2-phenyl-ethenyl)-5H-1,3,4-thiadiazolo[3,2-a]pyrimidine-5-one; and 2-(2-chloro-phenyl)-7-trans-(2-phenyl-ethenyl)-5H-1,3,4-thiadiazolo[3,2-a]pyrimidine-5-one.

EXAMPLE 6

(5-oxo-2-phenyl-5H-1,3,4-thiadiazolo[3,2-a]pyrimidine-7-yl)-methyl-triphenylphosphonium chloride, prepared according to Example 5 (6.3 g), was suspended in dimethylsulphoxide (20 ml) and treated dropwise with potassium terbutoxide (1.6 g) dissolved in dimethylsulphoxide (40 ml) at a temperature of about 25° C. The solution of the ylide so obtained was then reacted with 3-pyridinecarboxaldehyde (1.5 g) at room temperature for 10 minutes. After dilution with ice water containing NaH$_2$PO$_4$, the precipitate was filtered and washed with water: crystallization from methanol gave 2 g of 2-phenyl-7-trans-[2-(3-pyridyl)-ethenyl]-5H-1,3,4-thiadiazolo[3,2-a]pyrimidine-5-one, m.p. 279°–282° C., N.M.R. (CDCl$_3$—CF$_3$COOD) δp.p.m.: 7.02 (s) (1H, C-6 proton), 7.48 (d) (1H, β-ethenyl proton), 7.66 (m) (3H) and 7.95 (m) (2H) (phenyl protons), 7.9–8.2 (m) (3H, α-ethenyl proton, C-4 and C-5 pyridyl protons), 8.83 (bd) (1H, C-6 pyridyl proton), 9.10 (bs) (1H, C-2 pyridyl proton).

By proceeding analogously the following compounds were prepared:

2-(4-methyl-phenyl)-7-trans-[2-(3-pyridyl)-ethenyl]-5H-1,3,4-thiadiazolo[3,2-a]pyrimidine-5-one, m.p. 244°–246° C.;

2-(3-methyl-phenyl)-7-trans-[2-(3-pyridyl)-ethenyl]-5H-1,3,4-thiadiazolo[3,2-a]pyrimidine-5-one;

2-(2-methyl-phenyl)-7-trans-[2-(3-pyridyl)-ethenyl]-5H-1,3,4-thiadiazolo[3,2-a]pyrimidine-5-one;

2-(4-methoxy-phenyl)-7-trans-[2-(3-pyridyl)-ethenyl]-5H-1,3,4-thiadiazolo[3,2-a]pyrimidine-5-one, m.p. 258°–261° C.;

2-(3-methoxy-phenyl)-7-trans-[2-(3-pyridyl)-ethenyl]-5H-1,3,4-thiadiazolo[3,2-a]pyrimidine-5-one;

2-(2-methoxy-phenyl)-7-trans-[2-(3-pyridyl)-ethenyl]-5H-1,3,4-thiadiazolo[3,2-a]pyrimidine-5-one;

2-(4-chloro-phenyl)-7-trans-[2-(3-pyridyl)-ethenyl]-5H-1,3,4-thiadiazolo[3,2-a]pyrimidine-5-one, m.p. 273°–274° C.;

2-(3-chloro-phenyl)-7-trans-[2-(3-pyridyl)-ethenyl]-5H-1,3,4-thiadiazolo[3,2-a]pyrimidine-5-one;

2-(2-chloro-phenyl)-7-trans-[2-(3-pyridyl)-ethenyl]-5H-1,3,4-thiadiazolo[3,2-a]pyrimidine-5-one;

2-(4-fluoro-phenyl)-7-trans-[2-(3-pyridyl)-ethenyl]-5H-1,3,4-thiadiazolo[3,2-a]pyrimidine-5-one, m.p. 272°–273° C.;

2-(3-fluoro-phenyl)-7-trans-[2-(3-pyridyl)-ethenyl]-5H-1,3,4-thiadiazolo[3,2-a]pyrimidine-5-one;

2-(2-fluoro-phenyl)7-trans-[2-(3-pyridyl)-ethenyl]-5H-1,3,4-thiadiazolo[3,2-a]pyrimidine-5-one;

2-(2,4-dichloro-phenyl)-7-trans-[2-(3-pyridyl)-ethenyl]-5H-1,3,4-thiadiazolo[3,2-a]pyrimidine-5-one;

2-(3,4-dichloro-phenyl)-7-trans-[2-(3-pyridyl)-ethenyl]-5H-1,3,4-thiadiazolo[3,2-a]pyrimidine-5-one;

2-(4-nitro-phenyl)-7-trans-[2-(3-pyridyl)-ethenyl]-5H-1,3,4-thiadiazolo[3,2-a]pyrimidine-5-one, m.p. 175°–178° C.;

2-(3-nitro-phenyl)-7-trans-[2-(3-pyridyl)-ethenyl]-5H-1,3,4-thiadiazolo[3,2-a]pyrimidine-5-one;

2-(2-nitro-phenyl)-7-trans-[2-(3-pyridyl)-ethenyl]-5H-1,3,4-thiadiazolo[3,2-a]pyrimidine-5-one;

2-(3-N,N-dimethylamino-phenyl)-7-trans-[2-(3-pyridyl)-ethenyl]-5H-1,3,4-thiadiazolo[3,2-a]pyrimidine-5-one;

2-(4-N,N-dimethylamino-phenyl)-7-trans-[2-(3-pyridyl)-ethenyl]-5H-1,3,4-thiadiazolo[3,2-a]pyrimidine-5-one;

2-(4-hydroxy-phenyl)-7-trans-[2-(3-pyridyl)-ethenyl]-5H-1,3,4-thiadiazolo[3,2-a]pyrimidine-5-one;

2-(3-hydroxy-phenyl)-7-trans-[2-(3-pyridyl)-ethenyl]-5H-1,3,4-thiadiazolo[3,2-a]pyrimidine-5-one;

2-(2-thienyl)-7-trans-[2-(3-pyridyl)-ethenyl]-5H-1,3,4-thiadiazolo[3,2-a]pyrimidine-5-one, m.p. 308°–310° C.;

2-phenyl-7-trans-[2-(2-pyridyl)-ethenyl]-5H-1,3,4-thiadiazolo[3,2-a]pyrimidine-5-one;

2-phenyl-7-trans-[2-(4-pyridyl)-ethenyl]-5H-1,3,4-thiadiazolo[3,2-a]pyrimidine-5-one, m.p. 245°–246° C.;

2-phenyl-7-trans-[2-(6-methyl-2-pyridyl)-ethenyl]-5H-1,3,4-thiadiazolo[3,2-a]pyrimidine-5-one, m.p. 250°–251° C.;

2-(4-fluoro-phenyl)-7-trans-[2-(2-pyridyl)-ethenyl]-5H-1,3,4-thiadiazolo[3,2-a]pyrimidine-5-one;

2-(4-fluoro-phenyl)-7-trans-[2-(4-pyridyl)-ethenyl]-5H-1,3,4-thiadiazolo[3,2-a]pyrimidine-5-one; and 2-(4-fluoro-phenyl)-7-trans-[2-(6-methyl-2-pyridyl)-ethenyl]-5H-1,3,4-thiadiazolo[3,2-a]pyrimidine-5-one.

EXAMPLE 7

By proceeding according to Examples 1 and 2, starting from suitable substituted 7-chloromethyl-5H-1,3,4-thiadiazolo[3,2-a]pyrimidine-5-ones, the following compounds were prepared:

2-methyl-7-trans-(2-phenyl-ethenyl)-5H-1,3,4-thiadiazolo[3,2-a]pyrimidine-5-one, m.p. 196°–198° C.;

2-methyl-7-trans-[2-(3-pyridyl)-ethenyl]-5H-1,3,4-thiadiazolo[3,2-a]pyrimidine-5-one, m.p. 261°–264° C.;

2-methyl-7-trans-[2-(2,6-dichloro-phenyl)-ethenyl]-5H-1,3,4-thiadiazolo[3,2-a]pyrimidine-5-one;

2-ethyl-7-trans-(2-phenyl-ethenyl)-5H-1,3,4-thiadiazolo[3,2-a]pyrimidine-5-one;

2-methoxymethyl-7-trans-[2-(4-fluoro-phenyl)-ethenyl]-5H-1,3,4-thiadiazolo[3,2-a]pyrimidine-5-one, m.p. 191°–193° C.;

2-methoxymethyl-7-trans-[2-(3-pyridyl)-ethenyl]-5H-1,3,4-thiadiazolo[3,2-a]pyrimidine-5-one;

2-trifluoromethyl-7-trans-(2-phenyl-ethenyl)-5H-1,3,4-thiadiazolo[3,2-a]pyrimidine-5-one;

2-ethoxymethyl-7-trans-(2-phenyl-ethenyl)-5H-1,3,4-thiadiazolo[3,2-a]pyrimidine-5-one;

2-ethoxymethyl-7-trans-[2-(3-pyridyl)-ethenyl]-5H-1,3,4-thiadiazolo[3,2-a]pyrimidine-5-one;

2-methoxymethyl-7-trans-(2-phenyl-ethenyl)-5H-1,3,4-thiadiazolo[3,2-a]pyrimidine-5-one;

2-trifluoromethyl-7-trans-[2-(3-pyridyl)-ethenyl]-5H-1,3,4-thiadiazolo[3,2-a]pyrimidine-5-one;

2-ethyl-7-trans-[2-(3-pyridyl)-ethenyl]-5H-1,3,4-thiadiazolo[3,2-a]pyrimidine-5-one;

2-methyl-7-trans-[2-(1-methyl-2-pyrrolyl)-ethenyl]-5H-1,3,4-thiadiazolo[3,2-a]pyrimidine-5-one;

2-methoxymethyl-7-trans-[2-(1-methyl-2-pyrrolyl)-ethenyl]5H-1,3,4-thiadiazolo[3,2-a]pyrimidine-5-one;

2-chloro-7-trans-2-(4-fluoro-phenyl)-ethenyl]-5H-1,3,4-thiadiazolo[3,2-a]pyrimidine-5-one;

2-chloro-7-trans-[2-(3-fluoro-phenyl)-ethenyl]-5H-1,3,4-thiadiazolo[3,2-a]pyrimidine-5-one;

2-chloro-7-trans-[2-(2-fluoro-phenyl)-ethenyl]-5H-1,3,4-thiadiazolo[3,2-a]pyrimidine-5-one;

2-chloro-7-trans-[2-(4-chloro-phenyl)-ethenyl]-5H-1,3,4-thiadiazolo[3,2-a]pyrimidine-5-one;

2-chloro-7-trans-[2-(3-chloro-phenyl)-ethenyl]-5H-1,3,4-thiadiazolo[3,2-a]pyrimidine-5-one;

2-chloro-7-trans-[2-(3-pyridyl)-ethenyl]-5H-1,3,4-thiadiazolo[3,2-a]pyrimidine-5-one;

2-chloro-7-trans-[2-(2-thienyl)-ethenyl]-5H-1,3,4-thiadiazolo[3,2-a]pyrimidine-5-one, and 2-chloro-7-trans-(2-phenyl-ethenyl)-5H-1,3,4-thiadiazolo[3,2-a]pyrimidine-5-one.

EXAMPLE 8

7-chloromethyl-5H-1,3,4-thiadiazolo[3,2-a]pyrimidine-5-one (10 g), prepared according to Example 1, was reacted with sulfuryl chloride (7.5 g) in dichloroethane (150 ml) under stirring at 60° C. for 2 hours. After cooling the precipitate was filtered then was suspended in water (500 ml) and neutralized by treatment with 35% NaOH. Filtration and washings with water gave 6-chloro-7-chloromethyl-5H-1,3,4-thiadiazolo[3,2-a]pyrimidine-5-one, m.p. 193°–195° C. (7.5 g), which was reacted with triphenylphosphine (9.1 g) in acetonitrile (125 ml) under stirring at reflux temperature for 20 hours. After cooling the precipitate was filtered and washed with ethyl acetate to give (6-chloro-5-oxo-5H-1,3,4-thiadiazolo[3,2-a]pyrimidine-7-yl)-methyl-triphenylphosphonium chloride (16 g), which was suspended in dimethylsulphoxide (60 ml) and treated dropwise with potassium terbutoxide (3.6 g) dissolved in dimethylsulphoxide (30 ml) at a temperature of about 20° C. The solution of the ylide so obtained was then reacted with benzaldehyde (6 g) at 80° C. for 8 hours. After cooling the solution was diluted with ice water and the precipitate was filtered and washed with water. Crystallization from chloroform-ethanol gave 3.4 g of 6-chloro-7-trans-(2-phenyl-ethenyl)-5H-1,3,4-thiadiazolo[3,2-a]pyrimidine-5-one, m.p. 265°–270° C. dec., N.M.R. (CF$_3$COOD) $\delta$ p.p.m.: 7.45 (m) (3H, C-3, C-4 and C-5 phenyl protons), 7.53 (d) (1H, $\beta$-ethenyl proton), 7.66 (dd) (2H, C-2 and C-6 phenyl protons), 8.05 (d), (1H, $\alpha$-ethenyl proton), 9.02 (s) (1H, C-2 proton); $J_{H\alpha \uparrow H\beta} = 16$ Hz.

By proceeding analogously, using suitable aldehydes, the following compounds were prepared:

6-chloro-7-trans-[2-(3-pyridyl)-ethenyl]-5H-1,3,4-thiadiazolo[3,2-a]pyrimidine-5-one, m.p. 225°–230° C. dec.;

6-chloro-7-trans-[2-(2,6-dichloro-phenyl)-ethenyl]-5H-1,3,4-thiadiazolo[3,2-a]pyrimidine-5-one;

6-chloro-7-trans-[2-(2-thienyl)-ethenyl]-5H-1,3,4-thiadiazolo[3,2-a]pyrimidine-5-one;
6-chloro-7-trans-[2-(2-methyl-5-thiazolyl)-ethenyl]-5H-1,3,4-thiadiazolo[3,2-a]pyrimidine-5-one;
6-chloro-7-trans-[2-(1-methyl-2-pyrrolyl)-ethenyl]-5H-1,3,4-thiadiazolo[3,2-a]pyrimidine-5-one; and
6-chloro-7-trans-[2-(4-fluoro-phenyl)-ethenyl]-5H-1,3,4-thiadiazolo[3,2-a]pyrimidine-5-one.

EXAMPLE 9

By proceeding according to Example 8, starting from suitable substituted 7-chloromethyl-5H-1,3,4-thiadiazolo[3,2-a]pyrimidine-5-ones, the following compounds were prepared:
2,6-dichloro-7-trans-(2-phenyl-ethenyl)-5H-1,3,4-thiadiazolo[3,2-a]pyrimidine-5-one;
6-chloro-2-methyl-7-trans-(2-phenyl-ethenyl)-5H-1,3,4-thiadiazolo[3,2-a]pyrimidine-5-one;
6-chloro-2-ethyl-7-trans-(2-phenyl-ethenyl)-5H-1,3,4-thiadiazolo[3,2-a]pyrimidine-5-one;
6-chloro-2-phenyl-7-trans-(2-phenyl-ethenyl)-5H-1,3,4-thiadiazolo[3,2-a]pyrimidine-5-one;
6-chloro-2-methylthio-7-trans-(2-phenyl-ethenyl)-5H-1,3,4-thiadiazolo[3,2-a]pyrimidine-5-one;
6-chloro-2-methoxymethyl-7-trans-(2-phenyl-ethenyl)-5H-1,3,4-thiadiazolo[3,2-a]pyrimidine-5-one;
2-benzylthio-6-chloro-7-trans-(2-phenyl-ethenyl)-5H-1,3,4-thiadiazolo[3,2-a]pyrimidine-5-one;
6-chloro-2-methyl-7-trans-[2-(3-pyridyl)-ethenyl]-5H-1,3,4-thiadiazolo[3,2-a]pyrimidine-5-one;
6-chloro-2-phenyl-7-trans-[2-(3-pyridyl)-ethenyl]-5H-1,3,4-thiadiazolo[3,2-a]pyrimidine-5-one, m.p. 297°–299° C.;
2,6-dichloro-7-trans-[2-(3-pyridyl)-ethenyl]-5H-1,3,4-thiadiazolo[3,2-a]pyrimidine-5-one;
6-chloro-2-(4-fluoro-phenyl)-7-trans-[2-(3-pyridyl)-ethenyl]-5H-1,3,4-thiadiazolo[3,2-a]pyrimidine-5-one; and
2-benzylthio-6-chloro-7-trans-[2-(3-pyridyl)-ethenyl]-5H-1,3,4-thiadiazolo[3,2-a]pyrimidine-5-one.

EXAMPLE 10

7-chloromethyl-5H-1,3,4-thiadiazolo[3,2-a]pyrimidine-5-one (10 g), prepared according to Example 1, was dissolved in dimethylformamide (40 ml) and reacted with anhydrous potassium acetate (10 g) under stirring at room temperature for 20 hours. After dilution with ice water the precipitate was filtered and washed with water to give 7-acetoxymethyl-5H-1,3,4-thiadiazolo[3,2-a]pyrimidine-5-one (9.7 g) which was hydrolyzed by treatment with 37% HCl (50 ml) in dioxane (100 ml) under stirring at room temperature for 2 hours. The reaction mixture was diluted with acetone and the precipitate was filtered and then treated with aqueous Na₂HPO₄: filtration and washings with water until neutral gave 7-hydroxymethyl-5H-1,3,4-thiadiazolo[3,2-a]pyrimidine-5-one (6.2 g) which was reacted with dicyclohexylcarbodiimide (14.4 g) in benzene (90 ml) and dimethylsulphoxide (25 ml) in the presence of trifluoroacetic acid (1 ml) and pyridine (1.71 ml) under stirring at room temperature for 20 hours. After treatment with oxalic acid bihydrate (3.1 g) at room temperature, the precipitate of dicyclohexylurea was filtered of and the organic solution was evaporated in vacuo to dryness: the residue was purified over a SiO$_2$ column using chloroform: ethyl acetate=95:5 as eluent. The 7-formyl-5H-1,3,4-thiadiazolo[3,2-a]pyrimidine-5-one so obtained (2.5 g) was reacted with the ylide obtained by treatment of triphenylphosphonium-benzyl chloride (2.94 g) with 50% NaH (0.43 g), in dimethylsulphoxide (40 ml) at room temperature for 22 hours. After dilution with ice water the precipitate was filtered and washed with water: crystallization from CH$_2$Cl$_2$-ethanol gave 2.1 g of 7-trans-(2-phenyl-ethenyl)-5H-1,3,4-thiadiazolo[3,2-a]pyrimidine-5-one, m.p. 216°–218° C.

By proceeding analogously the following compounds were prepared:
7-trans-[2-(4-fluoro-phenyl)-ethenyl]-5H-1,3,4-thiadiazolo[3,2-a]pyrimidine-5-one, m.p 254°–256° C.;
2-phenyl-7-trans-[2-(3-pyridyl)-ethenyl]-5H-1,3,4-thiadiazolo[3,2-a]pyrimidine-5-one, m.p. 279°–282° C.;
2-(4-fluoro-phenyl)-7-trans-[2-(3-pyridyl)-ethenyl]-5H-1,3,4-thiadiazolo[3,2-a]pyrimidine-5-one, m.p. 272°–273° C.;
2-chloro-7-trans-(2-phenyl-ethenyl)-5H-1,3,4-thiadiazolo[3,2-a]pyrimidine-5-one; and
2-chloro-7-trans-[2-(4-fluoro-phenyl)-ethenyl]-5H-1,3,4-thiadiazolo[3,2-a]pyrimidine-5-one.

EXAMPLE 11

2-amino-5-phenyl-1,3,4-thiadiazole (10 g) was reacted with ethyl 2-chloro-acetoacetate (18.6 g) in polyphosphoric acid (100 g) under stirring at 100° C. for 2 hours. After cooling, dilution with ice water and neutralization with 35% NaOH, the precipitate was filtered and washed with water until neutral; crystallization from isopropyl alcohol gave 6-chloro-7-methyl-2-phenyl-5H-1,3,4-thiadiazolo[3,2-a]pyrimidine-5-one (16.9 g), which was reacted with N-bromo-succinimide (10.9 g, added portionwise) in benzene (200 ml) at the reflux temperature for 32 hours. After cooling the reaction mixture was diluted with ethyl acetate and treated with aqueous NaHCO$_3$ and then with water: the separated organic solution was evaporated in vacuo to dryness and the residue was crystallized from methanol to give 7-bromomethyl-6-chloro-2-phenyl-5H-1,3,4-thiadiazolo[3,2-a]pyrimidine-5-one (12.3 g), which was reacted with triphenylphosphine (8.6 g) in acetonitrile (700 ml) at the reflux temperature for 4 hours. After cooling and evaporation in vacuo of the solvent, the residue was purified with ethyl acetate to give (6-chloro-5-oxo-2-phenyl-5H-1,3,4-thiadiazolo[3,2-a]pyrimidine-7-yl)-methyl-triphenylphosphonium bromide (17.6 g), which was treated with aqueous NaHCO$_3$ under stirring at room temperature to give a precipitate of (6-chloro-5-oxo-2-phenyl-5H-1,3,4-thiadiazolo[3,2-a]pyrimidine-7-yl]-methylene-triphenyl-phosphorane.

This compound was filtered, washed with water, dried under vacuum at room temperature and then suspended (15.1 g) in dichloroethane (600 ml) and reacted with 3-pyridine-carboxaldehyde (2.6 g) at the reflux temperature for 3 hours. After cooling the organic solution was evaporated in vacuo to dryness: the residue was purified over a SiO$_2$ column using chloroform: methanol 98:2 as eluent. Crystallization of the recovered product from CH$_2$Cl$_2$-ethyl acetate gave 5.4 g of 6-chloro-2-phenyl-7-trans-[2-(3-pyridyl)-ethenyl]-5H-1,3,4-thiadiazolo[3,2-a]pyrimidine-5-one, m.p. 297°–299° C., N.M.R. (CDCl$_3$-CF$_3$COOD) δ p.p.m.: 7.4–8.2 (m) (8H; α- and β-ethenyl protons; phenyl protons; C-5 pyridyl proton), 8.80 (d) (2H, C-4 and C-6 pyridyl protons), 9.11 (bs) (1H, C-2 pyridyl proton).

By proceeding analogously, starting from suitable 6-substituted-7-methyl-5H-1,3,4-thiadiazolo[3,2-a]pyrimidine-5-ones, the following compounds were obtained:

6-fluoro-2-phenyl-7-trans-[2-(3-pyridyl)-ethenyl]-5H-1,3,4-thiadiazolo[3,2-a]pyrimidine-5-one;

6-fluoro-2-(4-fluoro-phenyl)-7-trans-[2-(3-pyridyl)-ethenyl]-5H-1,3,4-thiadiazolo[3,2-a]pyrimidine-5-one;

6-methoxy-7-trans-[2-(4-fluoro-phenyl)-ethenyl]-5H-1,3,4-thiadiazolo[3,2-a]pyrimidine-5-one;

6-methoxy-2-phenyl-7-trans-[2-(3-pyridyl)-ethenyl]-5H-1,3,4-thiadiazolo[3,2-a]pyrimidine-5-one;

6-methoxy-2-(4-fluoro-phenyl)-7-trans-[2-(3-pyridyl)-ethenyl]-5H-1,3,4-thiadiazolo[3,2-a]pyrimidine-5-one;

6-acetoxy-2-phenyl-7-trans-[2-(3-pyridyl)-ethenyl]-5H-1,3,4-thiadiazolo[3,2-a]pyridine-5-one;

6-acetoxy-2-(4-fluoro-phenyl)-7-trans-[2-(3-pyridyl)-ethenyl]-5H-1,3,4-thiadiazolo[3,2-a]pyrimidine-5-one;

6-fluoro-7-trans-(2-phenyl-ethenyl)-5H-1,3,4-thiadiazolo[3,2-a]pyrimidine-5-one;

6-acetoxy-7-trans-(2-phenyl-ethenyl)-5H-1,3,4-thiadiazolo[3,2-a]pyrimidine-5-one; and 6-methoxy-7-trans-(2-phenyl-ethenyl)-5H-1,3,4-thiadiazolo[3,2-a]pyrimidine-5-one.

EXAMPLE 12

2-(4-nitro-phenyl)-7-trans-[2-(3-pyridyl)-ethenyl]-5H-1,3,4-thiadiazolo[3,2-a]pyrimidine-5-one, (5.7 g), was reacted with $SnCl_2.2H_2O$ (33.7 g) in 37% HCl (25 ml) and acetic acid (80 ml) under stirring at 60° C. for 4 hours. After cooling the precipitate was filtered and washed with water and then suspended under stirring in 2N NaOH: the product was filtered, washed with water until neutral and then crystallized from chloroform-ethanol to give 2.8 g of 2-(4-amino-phenyl)-7-trans-[2-(3-pyridyl)-ethenyl]-5H-1,3,4-thiadiazolo[3,2-a]pyrimidine-5-one, m.p. 322°–325° C., N.M.R. (DMSO $d_6$) δ p.p.m.: 6.16 (bs) (2H, —$NH_2$), 6.42 (s) (1H, C-6 proton), 6.65 (bd) (2H, C-3 and C-5 phenyl protons), 7.32 (d) (1H, β-ethenyl proton), 7.43 (dd) (1H, C-5 pyridyl proton), 7.60 (bd) (2H, C-2 and C-6 phenyl protons), 7.72 (d) (1H, α-ethenyl proton), 8.11 (ddd) (1H, C-4 pyridyl proton), 8.50 (dd) (1H, C-6 pyridyl proton), 8.83 (d) (1H, C-2 pyridyl proton).

By proceeding analogously the following compounds were obtained:

2-(3-amino-phenyl)-7-trans-[2-(3-pyridyl)-ethenyl]-5H-1,3,4-thiadiazolo[3,2-a]pyrimidine-5-one;

2-(2-amino-phenyl)-7-trans-[2-(3-pyridyl)-ethenyl]-5H-1,3,4-thiadiazolo[3,2-a]pyrimidine-5-one; and 7-trans-[2-(4-amino-phenyl)-ethenyl]-5H-1,3,4-thiadiazolo[3,2-a]pyrimidine-5-one.

EXAMPLE 13

2-(4-amino-phenyl)-7-trans-[2-(3-pyridyl)-ethenyl]-5H-1,3,4-thiadiazolo[3,2-a]pyrimidine-5-one (1 g), was reacted with acetic anhydride (4 ml) and pyridine (4 ml) in dimethylformamide (25 ml) at 140° C. for 13 hours. Dilution with ice water gave a precipitate, which was filtered and washed with water: crystallization from dimethylformamide-ethanol gave 0.85 g of 2-(4-acetylamino-phenyl)-7-trans-[2-(3-pyridyl)-ethenyl]-5H-1,3,4-thiadiazolo[3,2-a]pyrimidine-5-one, m.p. 380°–383° C.

By proceeding analogously the following compounds were prepared:

2-(3-acetylamino-phenyl)-7-trans-[2-(3-pyridyl)-ethenyl]-5H-1,3,4-thiadiazolo[3,2-a]pyrimidine-5-one;

2-(2-acetylamino-phenyl)-7-trans-[2-(3-pyridyl)-ethenyl]-5H-1,3,4-thiadiazolo[3,2-a]pyrimidine-5-one; and 7-trans-[2-(4-acetylamino-phenyl)-ethenyl]-5H-1,3,4-thiadiazolo[3,2-a]pyrimidine-5-one.

EXAMPLE 14

7-trans-[2-(4-hydroxy-phenyl)-ethenyl]-5H-1,3,4-thiadiazolo[3,2-a]pyrimidine-5-one, (1 g), was reacted with acetic anhydride (2 ml) in pyridine (4 ml) at room temperature for 20 hours. Dilution with ice water gave a precipitate, which was filtered and washed with water: crystallization from methanol gave 0.78 g of 7-trans-[2-(4-acetoxy-phenyl)-ethenyl]-5H-1,3,4-thiadiazolo[3,2-a]pyrimidine-5-one, m.p. 249°–251° C.

By proceeding analogously the following compounds were prepared:

2-(3-acetoxy-phenyl)-7-trans-[2-(3-pyridyl)-ethenyl]-5H-1,3,4-thiadiazolo[3,2-a]pyrimidine-5-one; and 2-(4-acetoxy-phenyl)-7-trans-[2-(3-pyridyl)-ethenyl]-5H-1,3,4-thiadiazolo[3,2-a]pyrimidine-5-one.

EXAMPLE 15

2-phenyl-7-trans-[2-(3-pyridyl)-ethenyl]-5H-1,3,4-thiadiazolo[3,2-a]pyrimidine-5-one (2 g), dissolved in dioxane (200 ml) was treated with the stoichiometric amount of gaseous HCl at room temperature. The precipitate was filtered and washed with dioxane to give 1.9 g of 2-phenyl-7-trans-[2-(3-pyridyl)-ethenyl]-5H-1,3,4-thiadiazolo[3,2-a]pyrimidine-5-one, hydrochloride, m.p. 260° C. dec.

By proceeding analogously the hydrochlorides of the compounds obtained in Examples from 1 up to 14 were prepared.

EXAMPLE 16

Tablets, each weighing 200 mg and containing 100 mg of the active substance are manufactured as follows:

| Compositions (for 10000 tablets) | |
| --- | --- |
| 2-phenyl-7-trans-[2-(3-pyridyl)-ethenyl]-5H—1,3,4-thiadiazolo[3,2-a]pyrimidine-5-one | 1000 g |
| Lactose | 710 g |
| Corn starch | 237.5 g |
| Talc powder | 37.5 g |
| Magnesium stearate | 15 g |

2-phenyl-7-trans-[2-(3-pyridyl)-ethenyl]-5H-1,3,4-thiadiazolo[3,2-a]pyrimidine-5-one, lactose and a half of the corn starch are mixed; the mixture is then forced through a sieve of 0.5 mm openings.

Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

EXAMPLE 17

Tablets, each weighing 200 mg and containing 100 mg of the active substance are manufactured as follows:

| Compositions (for 10000 tablets) | |
| --- | --- |
| 7-trans-[2-(4-fluoro-phenyl)-ethenyl]-5H—1,3,4-thiadiazolo[3,2-a]pyrimidine-5-one | 1000 g |

| Compositions (for 10000 tablets) | |
|---|---|
| Lactose | 710 g |
| Corn starch | 237.5 g |
| Talc powder | 37.5 g |
| Magnesium Stearate | 15 g |

7-trans-[2-(4-fluoro-phenyl)-ethenyl]-5H-1,3,4-thiadiazolo[3,2-a]pyrimidine-5-one, lactose and a half of the corn starch are mixed; the mixture is then forced through a sieve of 0.5 mm openings.

Corn starch (18 g) is suspended in warm water (180 ml). The resulting paste is used to granulate the powder. The granulates are dried, comminuted on a sieve of sieve size 1.4 mm, then the remaining quantity of starch, talc and magnesium stearate is added, carefully mixed and processed into tablets using punches of 8 mm diameter.

We claim:

1. A compound of formula (I)

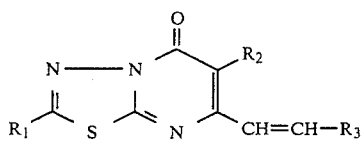

wherein
R₁ is
 (a) hydrogen or halogen;
 (b) a $C_1$-$C_6$ alkyl group, unsubstituted or substituted by $C_1$-$C_4$ alkoxy or by halogen;
 (c) a phenyl ring unsubstituted or substituted by a group chosen from halogen, $C_1$-$C_4$ alkyl and $C_1$-$C_4$ alkoxy;
 (d) a $C_1$-$C_6$ alkylthio group;
R₂ is hydrogen or halogen;
R₃ is 2-pyridyl, 3-pyridyl or 4-pyridyl, wherein each pyridyl group is unsubstituted or substituted by $C_1$-$C_4$ alkyl; and the pharmaceutically acceptable salts thereof.

2. A compound of formula (I), according to claim 1, wherein:
R₁ is hydrogen, chlorine, methyl, ethyl, methylthio, ethylthio, trifluoromethyl, methoxymethyl, ethoxymethyl, a phenyl ring unsubstituted or substituted by one or two substituents chosen from methyl, methoxy, chlorine and fluorine;
R₂ is hydrogen, fluorine or chlorine;
R₃ is 2-pyridyl, 3-pyridyl or 4-pyridyl wherein each pyridyl group is unsubstituted or substituted by a methyl group, and the pharmaceutically acceptable salts thereof.

3. A compound selected from the group consisting of:
2-phenyl-7-trans-[2-(3-pyridyl)-ethenyl]-5H-1,3,4-thiadiazolo[3,2-a]pyrimidine-5-one;
7-trans-[2-(3-pyridyl)-ethenyl]-5H-1,3,4-thiadiazolo[3,2-a]pyrimidine-5-one; and
2-methyl-7-trans-[2-(3-pyridyl)-ethenyl]-5H-1,3,4-thiadiazolo[3,2-a]pyrimidine-5-one; and the pharmaceutically acceptable salts thereof.

* * * * *